(12) United States Patent
Bauer

(10) Patent No.: US 6,589,507 B1
(45) Date of Patent: Jul. 8, 2003

(54) FOAMING ANTACID SUSPENSION TABLETS

(75) Inventor: Kurt H. Bauer, Freiburg (DE)

(73) Assignee: DR. Regenold GmbH, Badenweiler (DE)

( * ) Notice: Subject to any disclaimer, the term of this patent is extended or adjusted under 35 U.S.C. 154(b) by 0 days.

(21) Appl. No.: 09/868,556

(22) PCT Filed: Dec. 14, 1999

(86) PCT No.: PCT/EP99/09934

§ 371 (c)(1),
(2), (4) Date: Aug. 13, 2001

(87) PCT Pub. No.: WO00/37043

PCT Pub. Date: Jun. 29, 2000

(30) Foreign Application Priority Data

Dec. 21, 1998 (DE) .......................................... 198 59 231

(51) Int. Cl.⁷ ................................................. A61C 9/04
(52) U.S. Cl. ......................................... 424/44; 514/819
(58) Field of Search ............................. 424/44; 514/819

(56) References Cited

U.S. PATENT DOCUMENTS 4,613,497 A * 9/1986 Chavkin ...................... 424/44
4,716,033 A 12/1987 Denick, Jr. .................. 424/48
4,783,331 A 11/1988 Alexander et al. ............ 424/44
5,330,760 A 7/1994 Walton ....................... 424/466

* cited by examiner

*Primary Examiner*—Alton N. Pryor
(74) *Attorney, Agent, or Firm*—Hamilton, Brook, Smith & Reynolds, P.C.

(57) ABSTRACT

The invention relates to antacid preparations comprising the following constituents:

(i) an acid-binding active constituent (antacid) or a mixture of such active constituents,
(ii) an effervescent mixture that releases $CO_2$,
(iii) a polymeric surfactant as foam-forming agent or a mixture of such surfactants,
(iv) a swellable and gel-forming polymer or a mixture of such polymers, and
(v) optionally conventional auxiliary substances, as well as a process for the production of such antacid preparations. In a particularly preferred embodiment the antacid preparation is formulated in the form of a chewable tablet. The antacid preparations according to the invention are suitable for the symptomatic treatment of duodenal ulcers, gastric ulcers, as well as heartburn and acid-caused gastric disorders such as hyperacidic gastritis.

11 Claims, 1 Drawing Sheet

FOAMING ANTACID SUSPENSION TABLETS

This Application is a 371 of PCT/EP99/09934 filed Dec. 14, 1999.

DESCRIPTION

The present invention relates to preparations that contain one or more acid-binding active constituents (antacids), as well as a process for the production of these preparations and their use as medicaments for the regulation of gastric hyperacidity.

Therapy with antacids has proved outstandingly successful for the treatment of a number of acute and chronic gastro-intestinal conditions. In particular, antacids are used for the symptomatic treatment of duodenal and gastric ulcers as well as in heartburn and acid-caused gastric disorders such as hyperacidic gastritis. The action of the antacids basically depends on the fact that the gastric hydrochloric acid is to some extent buffered so that the pH of the stomach is increased from 1 to 2 or 3, or even 4. Due to this increase in the pH value the symptoms typical of hyperacidity, such as for example a feeling of fullness or heartburn, are reduced or even eliminated. Up to now antacids have been marketed and sold in powder form, as normal tablets, predominantly as chewable tablets or as suspensions in bottles or packed in sachets. In German patent application DE 44 24 676 antacid effervescent tablets are also described.

The known chewable tablets can be administered extremely easily and simply, but have the disadvantage that the patient finds that these tablets are chalky and thus unpleasant after they have been chewed. In contrast to this the known, finely dispersed suspension medicament forms are not perceived as being chalky, are well tolerated, and are furthermore characterised by a rapid and clearly detectable onset of action and effect. The disadvantage of these suspension medicament forms is however the fact that elderly patients in particular have difficulty in removing the suspensions completely and without too much effort from the sachet packagings. On the other hand the formulation and administration of effervescent tablets is simpler, although the effervescent tablets used up to now have to be taken with a glass of water, in which the effervescent tablets dissolve with foaming to form a liquid drinkable suspension. For this reason it is not possible to take the medicament at every opportunity. Accordingly, all the hitherto available preparation forms of antacids have certain disadvantages as regards their administration.

The object of the present invention is to provide an antacid preparation with which an effective and rapidly acting suspension can be produced in as uniformly fine a dispersity as possible, for example preferably by chewing and insalivation, wherein the antacid preparation can at the same time be administered in a better, more reliable and more uncomplicated manner than the antacid formulations knows from the prior art.

This object is achieved by the features disclosed in the patent claims.

In particular the present invention relates to antacid chewable tablets that develop a foam gel when chewed in the mouth. Such tablets can be produced so that they can also still easily be chewed by elderly patients. Chewable tablets permit a satisfactory dosage of the active constituents, are easy to remove from their packagings and do not require any liquid when they are taken. The novel tablets according to the invention develop, when chewed and mixed with saliva, a foaming suspension gel that is discerned as pleasant in the mouth and can be swallowed without any problem. This highly dispersed foam gel leads to a surprisingly good buffering in the stomach.

The invention relates to an antacid preparation that comprises the following constituents:

(i) an acid-binding active constituent (antacid) or a mixture of such active constituents, (ii) an effervescent mixture that releases $CO_2$, (iii) a polymeric surfactant as foam-forming agent or a mixture of such surfactants, (iv) a swelling and gel-forming polymer or a mixture of such polymers, and (v) optionally conventional auxiliary substances.

Acid-binding active constituents for antacid preparations are known to the person skilled in the art. Particularly suitable as acid-binding active constituents are magnesium hydroxide, magnesium oxide, magnesium carbonate, magnesium silicate, aluminium hydroxide, aluminium phosphate and magnesium aluminium silicate or mixtures thereof. Preferred active constituents are aluminium hydroxide, magnesium hydroxide, hydrotalcite or magaldrate, which is a magnesium-aluminium silicate. Magaldrate is particularly preferred. It is know to the person skilled in the art from DE 44 24 676 for example that aluminium containing medicaments can have a toxic effect under certain conditions, in particular if the aluminium compound is administered jointly with certain acids, for example citric acid. In the choice of the aforementioned possible acid-binding active constituents the person skilled in the art will accordingly be governed by the overall composition of the antacid preparation and for example will not use, or use only in relatively minor amounts, aluminium compounds if another constituent of the preparation according to the invention is citric acid, or conversely the person skilled in the art will not use citric acid, or only in relatively minor amounts, if the preparation is to contain an aluminium compound.

The acid-binding active constituents are used according to the invention in a concentration of 20 to 80 wt. %, preferably 40 to 75 wt. %, more preferably 50 to 70 wt. %, referred to the total dry weight of the preparation.

The effervescent mixture that releases $CO_2$ and that is used includes an acid constituent as well as a basic constituent. Suitable as acid constituents of the $CO_2$-developing effervescent mixture are for example citric acid, tartaric acid, adipic acid, ascorbic acid, malic acid, fumaric acid and maleic acid, as well as acid salts, for example potassium bitartrate, primary sodium phosphate, primary sodium citrate, primary sodium tartrate or mixtures thereof. Preferred are citric acid, tartaric acid, adipic acid and primary sodium citrate; particularly preferred are citric acid, tartaric acid and primary sodium citrate. As previously mentioned the person skilled in the art will, when selecting the acid to be used as acid constituent of the $CO_2$-developing effervescent mixture, bear in mind the overall formulation of the preparation and will in particular avoid the use of certain acids if thereby there is a risk of an increased toxicity of the acid-binding active constituents.

Further suitable acid components of the $CO_2$-developing effervescent mixture are acid salts of basic amino acids such as glycine, alanine, valine, ornithine or lysine.

Suitable as basic constituents of the effervescent mixture are that release $CO_2$, in general compounds that develop $CO_2$, in particular sodium hydrogen carbonate, sodium carbonate, calcium carbonate or mixtures thereof.

The ratio of the acid constituent of the $CO_2$-developing effervescent mixture to the basic constituent of the $CO_2$- developing effervescent mixture is as a rule equimolecular/ stoichiometric. Since however the antacid-acting medicaments too react basically, it may be necessary for reasons of buffering or taste (adjustment of an optimal pH value) to add the acid component in excess.

The proportion of the effervescent mixtures that release $CO_2$ in the total dry weight of the antacid preparation is 5 to 50 wt. %, preferably 7.5 to 25 wt. %, most particularly preferably 10 to 20 wt. %. For the formulation as an antacid chewable tablet that develops a foam gel when chewed in the mouth, the constituents of the effervescent mixture are preferably calculated stoichiometrically in such as way that the foam suspension gel formed in the mouth by the remaining constituents and saliva reacts in a weakly alkaline manner. The expression weakly alkaline is understood to mean a pH of 7 to 9, preferably 7 to 8.

If the antacid preparation is formulated as a chewable tablet,then the effervescent mixtures that release $CO_2$ in the foaming suspension tablets according to the invention are in principle employed in significantly smaller amounts than in effervescent tablets. They should in fact produce no liquid suspension, but instead an easily swallowable foam gel that releases the active constituents rapidly and in a finely dispersed manner in the stomach over large areas of the gastric mucosa.

As polymeric, foam-forming surfactant ("foam-forming agent") for the preparations according to the invention, there may be used in particular highly compatible polymeric surfactants, such as for example poloxamers (block copolymers of ethylene oxide and propylene oxide), or other non-toxic polymeric surfactants having molecular weights of more than 3000. Particularly preferred are Pluronic® F 68 or Pluronic® F 127 (BASF AG Ludwigshafen/Rhine, or Wyandotte Chem. Corp., Biddle, Wyandotte, Mich.), which are not or are only slightly haemolytic (damage the blood corpuscles). The content of the foam-forming polymeric ten-sides
in the preparation is 0.5 to 30 wt. %, preferably 1 to 20 wt. %, most particularly preferably 3 to 10 wt. %, referred to the total dry weight of the preparation.

Suitable as swelling and gel-forming polymer are in particular polysaccharides and polysaccharide derivatives, as well as polyacrylic acids. Examples of polysaccharides and polysaccharide derivatives include gum tragacanth, galactomannan, cellulose ethers, for example methylcellulose, and mixed cellulose ethers such as hydroxypropylmethyl or hydroxybutylmethyl cellulose. Such methylcellulose ethers and mixed cellulose ethers are marketed by Dow Chemical under the trade name Methocel®. Examples of polyacrylic acids that may be used according to the invention are Carbopol® or Eudispert® (pharmaceutically conventional and/or allowed types of Carbopol® or Eudispert®). The proportion of the swelling, gel-forming polymers in the total dry weight of the preparation is 3 to 30%, preferably 5 to 15%, most particularly preferably 7.5 to 10%.

The antacid preparation as a rule has a residual moisture content of not more than 6%, preferably not more than 3%, most particularly preferably not more than 1%, referred to the total weight of the preparation.

The antacid preparation may in addition also contain conventional tablet auxiliary substances, such as for example sugar alcohols or sugars (glucose, lactose, etc.) as fillers, sweetening agents, flavouring agents, as well as lubricants, mould release agents and flow regulation agents.

The preparation according to the invention is suitable for use as an antacid, i.e. as a medicament for regulating the hyperacidity of the stomach. The preparations according to the invention may in this connection be formulated in particular in the form of a chewable tablet. Other forms of administration are however also possible, such as for example administration in the form of a powder or granules.

The present invention furthermore provides a process for the production of a preparation as defined above, which comprises the following steps:

(i) homogeneous mixing of an acid-binding active constituent or mixtures thereof with the basic constituent of the effervescent mixture that releases $CO_2$, as well as optionally with one or more swelling, gel-forming polymers, (ii) production of a solution/suspension that contains one or more foam-forming agents as well as optionally a swelling, gel-forming polymer or mixtures of such polymers, (iii) combining and mixing of the homogeneous mixture obtained in (i) with the suspension/solution obtained in (ii), wet granulating on of the mixture, as well as drying and screening of the granules obtained, (iv) production of a homogeneous dry mixture from the acid constituent of the effervescent mixture that releases $CO_2$ and optionally one or more swelling, gel-forming polymers, (v) mixing of the mixture obtained in (iv) with the granules obtained in (iii) and optionally pressing of the granules obtained into tablets, wherein the swelling, gel-forming polymer is homogeneously mixed in in at least one of the steps (i), (ii) or (iv) and wherein conventional tablet auxiliary substances can also be added in the individual process steps.

In the first step (i) of the process according to the invention the acid-binding active constituent or a mixture of these active constituents is homogeneously mixed with the basic constituent of the effervescent mixture releasing $CO_2$. Optionally a swelling, gel-forming polymer or a mixture of several of these polymers may already be added at this stage. The homogeneous mixing may preferably be carried out by means of an intensive mixer or kneader mixer.

In parallel to this an aqueous solution of the foam-forming agent, for example an aqueous solution of Pluronic® F 68 or Pluronic® F 127, is prepared as step (ii). Water or an aqueous surfactant solution or sweetening agent solution, for example a poloxamer or saccharine solution, may be used as aqueous solvent. At least so much aqueous solution is used that the foam-forming agent(s) to be used still just dissolve. Preferably the amount of water used is just sufficiently high that the relevant mass is moist-plastic and can be granulated sufficiently well. A swelling, gel-forming polymer or mixtures thereof may optionally be added to the aqueous solution of the foam-forming agent. A homogeneous suspension is formed by stirring.

In a third step (iii) the homogeneous mixture of acid-binding active constituent or mixtures thereof and the basic constituent of the effervescent mixture that releases $CO_2$, obtained in step (i), which optionally in addition contains one or more swelling gel-forming polymers, is combined and mixed with the aqueous solution of the foam-forming agent and/or with the aqueous suspension of the foam-forming agent and the swelling gel-forming polymers or mixtures thereof obtained in step (ii). A mixer or kneader with stirrers or kneading devices is used for mixing these constituents. After the combination and mixing, the mixture that is obtained is wet granulated. The wet granulating is carried out by adding liquid until the mixture is of a moist plastic and thus granulable consistency. After the wet granulating the granules obtained are dried. In this connection the drying is carried out to a residual moisture content of 0.1 to 6.0%, preferably 1 to 3%, most particularly preferably <1.0%. Conventional drying equipment such as drying cabinets and fluidized-bed dryers may be used as dryers. Suitable dryers are described for example in Bauer, Frömming, Führer, "Pharmazautische Technologie", G. Fischer Verlag, Stuttgart, Jena, 5$^{th}$ Edition, 1997, pp. 123 to 130. The preliminary drying is preferably carried out at temperatures of 30° to 70° C., more preferably 40° to 60° C., and most preferably at 45° to 50° C.

The dried granules are then screened. Conventional screens such as are described for example in Bauer, Frömming, Führer, "Pharmazautische Technologie", G. Fischer Verlag, Stuttgart, Jena, 5$^{th}$ Edition, 1997, p. 108 (screens) may conveniently be used as screens. Suitable screens have a mesh width of 0.1 to 3.0 mm, preferably 0.5 to 1.5 mm. The screening is carried out at normal pressure or optionally under excess pressure. The suitable screen mesh widths depend on the desired and/or required dispersity or homogeneity.

In the fourth step (iv) a homogeneous dry mixture is prepared from the acid constituent of the effervescent mixture that releases $CO_2$ and optionally one of the several swelling gel polymers. To produce this homogeneous dry mixture the same equipment may be used as was described above for the first step of the process.

In the next step (v) the mixture of the acid constituent of the effervescent mixture that releases $CO_2$ and optionally one or more gel-forming polymers obtained in step (iv) is mixed into the granules obtained in the third step. For the mixing the same apparatus for example may be used as described for the first step. The granules thus obtained may then be compressed for example into chewable tablets. Preferably the tablets are compressed sufficiently hard that they can easily be packaged but are still easily chewable. The known rotary pelleting machines and eccentric pelleting machines are suitable as pelleting devices. The hardness of the chewable foam gel tablets should preferably be 4 to 7 kp.

In the process according to the invention conventional tablet auxiliary substances, such as for example the auxiliary substances defined above, may be added as necessary at each of the steps. The swelling, gel-forming polymer must be mixed in in at least one of the steps (i), (ii) or (iv). In a particularly preferred embodiment the swelling, gel-forming polymer is added at steps (ii) and (iv). In another preferred embodiment the swelling, gel-forming polymer is simply added at step (i). In a yet further preferred embodiment the swelling, gel-forming polymer is simply added at step (iv). In this connection care should be taken to ensure that acid and basic reacting substances are mixed as such or in a state such that they cannot react prematurely or unintentionally. This is ensured for example by granulating them separately and mixing them only in a dry, non-reactive state.

The preparations produced by the process according to the invention may be formulated as a chewable tablet. In the stomach the highly dispersed foam gel formed after chewing in the mouth in combination with saliva leads, as shown in FIG. 1, to a surprisingly rapid buffering. The buffer capacities are between those of a normal aluminium hydroxide gel/magnesium hydroxide gel suspension and a normal aluminium hydroxide gel/magnesium hydroxide gel tablet. The invention is illustrated in more detail with the aid of FIG. 1 and the following examples:

EXAMPLES

Example 1

Figure 1:
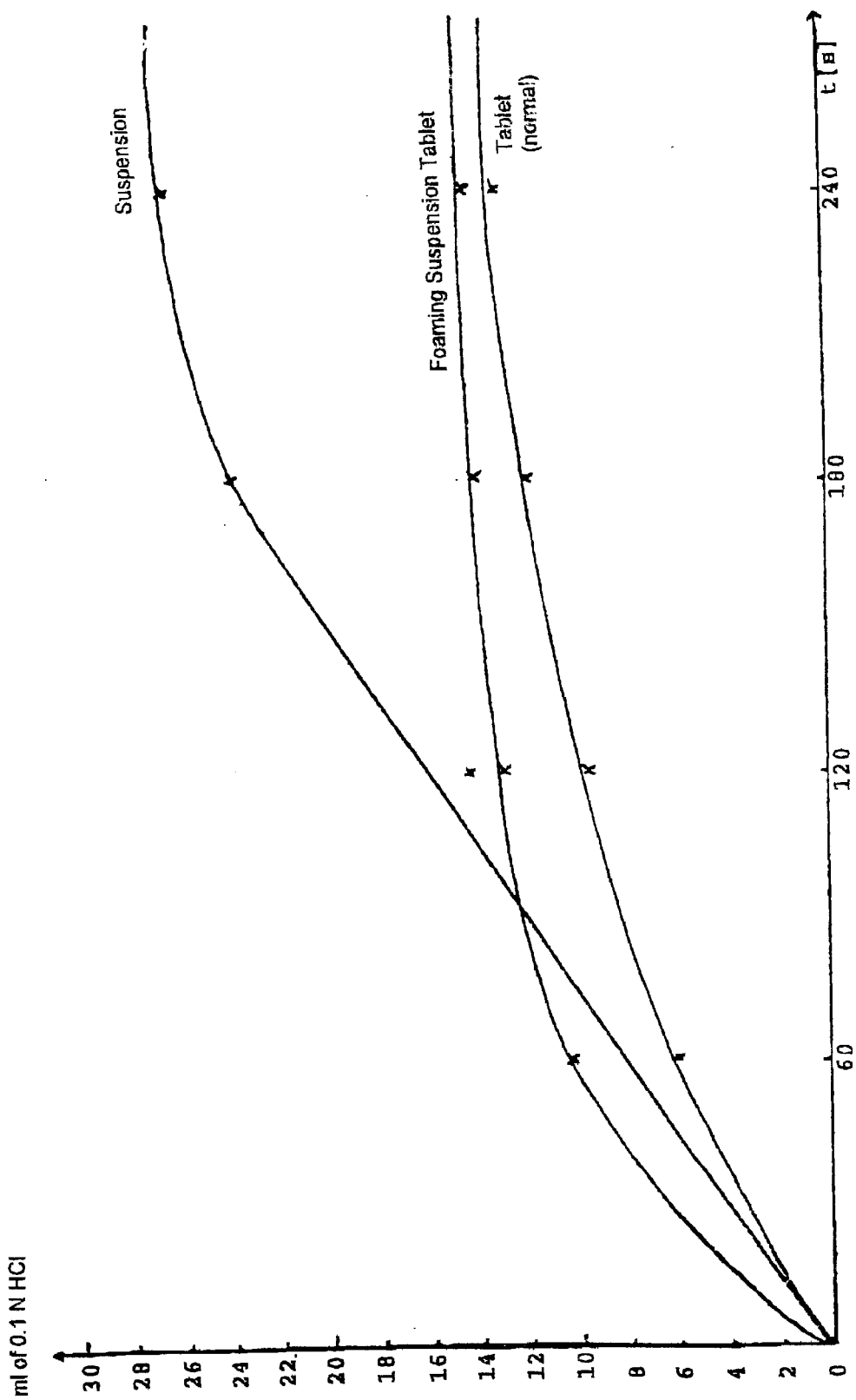
FIG. 1 shows the determination of the buffer capacity by direct titration of selected antacid preparations with 0.1 N HCl in ml/sec.

40.0 g of aluminium oxide dry gel, 40.0 g of magnesium oxide dry gel, 10.0 g of sodium hydrogen carbonate and 10.0 g of heavy basic magnesium carbonate are homogeneously mixed. 0.1 g of saccharine sodium and 30.0 g of Poloxamer 188 (Pluronic® F 68) are dissolved in 50 to 60 ml of warm water, following which 3.0 g of Methocel® are suspended free of lumps in this solution. On cooling, the Methocel® dissolves practically quantitatively. The mixture of the active constituents together with the carbonates is wet granulated with the resultant solution and then dried at 45° C. and screened. 12.0 g of Methocel®, 15.0 g of anhydrous citric acid, 18.2 g of mannitol, 1.5 g of magnesium stearate and 0.2 g of flavouring agent are then homogeneously dry mixed and this mixture is added as external phase to the previously obtained granules. The granules are compressed into tablets of 1800.0 mg gross weight and diameter 16 mm.

Example 2

40.0 g of aluminium hydroxide gel, 40.0 g of magnesium hydroxide gel, 20.0 g of sodium hydrogen carbonate and 15.0 g of sodium carboxymethylcellulose are homogeneously mixed. This mixture is wet granulated with a solution of 0.1 g of saccharine sodium and 40.0 g of poloxamer 407 (Pluronic® F 127) in 70 to 80 ml of water, dried at 40° C., and screened. 20.0 g of citric acid (anhydrous/anhydrate), 18.1 g of lactose (DAB/EuAB), 1.5 g of magnesium stearate (DAB/EuAB) and 0.3 g of wild raspberry flavouring agent are then mixed in as external phase. The granules are compressed into tablets of 18 mm diameter and having a gross weight of 1950.0 mg.

Example 3

750.0 g of magaldrate, 150.0 g of calcium carbonate and 150.525 g of xylitol are homogeneously mixed and screened. The resulting mixture is kneaded in a known manner with a solution of 0.975 g of saccharine sodium, 9.0 g of cyclamate sodium and 90.0 g of Pluronic® F 68 in 300.0 to 450.0 ml of water, wet granulated (2 mm screen) and dried at 60° C. (residual moisture 4% to 6%). After drying, 105.0 g of citric acid anhydrate, 9.75 g of magnesium stearate, 25.0 g of polyacrylic acid and 9.75 g of orange flavouring agent are mixed in with these granules as external phase, following which the granules are tabletted in a manner known per se.

Example 4

750.0 g of magaldrate (co-dried), 250.0 g of sodium carbonate/sodium hydrogen carbonate and 145.025 g of glucose are homogeneously mixed and screened. The resulting mixture is kneaded in a manner known per se with a solution of 0.975 g of saccharine sodium, 9.0 g of cyclamate sodium and 120.0 g of Pluronic® F 127 in 300.0 to 400.0 ml of water, wet granulated (2 mm screen), and dried at 45° C. (residual moisture 5% to 8%). After drying, 105.0 g of tartaric acid, 12.0 g of magnesium stearate, 8.0 g of flavouring agent and 100.0 g of sodium carboxymethyl starch are mixed in with these granules as external phase, following which the granules are tabletted in a manner known per se.

Example 5

500.0 g of hydrotalcite, 120.0 g of sodium carbonate and 103.2 g of mannitol are homogeneously mixed and screened (1 mm screen). The resultant mixture is kneaded in a manner known per se with a solution of 0.8 g of saccharine sodium, 8.0 g of cyclamate sodium and 80.0 g of Pluronic® F 127 in 250.0 to 300.0 ml of water, wet granulated (2 mm screen), and dried at 60° C. (residual moisture 4% to 6%). After drying, 90.0 g of citric acid anhydrate/sodium citrate primary, 10.0 g of calcium arachinate and 80.0 g of hydroxypropylcellulose and 8.0 g of flavouring agent are mixed into these granules as external phase, following which the granules are tabletted in a manner known per se. This formulation can be used to produce 500.0 mg or 1000.0 mg tablets. Tablet diameters should be chosen so as to ensure that the tablets are not too thick and therefore difficult to chew.

Example 6

Determination of the buffer capacity of the foaming antacid suspension tablets according to the invention.

The buffer capacity of an antacid suspension obtainable as a proprietary product, of an antacid tablet obtainable as a proprietary product, and of a foaming antacid suspension tablet according to the invention were compared to one another. All preparations contained the same amount of active constituent. The buffer capacity was determined by direct titration of the aforementioned preparations with 0.1 N HCl. The experiment shows that the foaming antacid suspension tablets according to the invention buffer acid significantly better than conventional tablets. Conventional liquid suspensions exhibit overall the best buffer capacity, the suspensions initially being slower to exert a buffer effect than the foaming antacid suspensions tablets according to the invention. The results of this experiment are shown graphically in FIG. 1.

What is claimed is:

1. Antacid preparation comprising the following constituents:
    (i) an acid-binding active constituent (antacid) or a mixture of said active constituents,
    (ii) an effervescent mixture that releases $CO_2$,
    (iii) a polymeric surfactant selected from poloxamers as foam-forming agent or a mixture of said surfactants,
    (iv) a swelling and gel-forming polymer different from the component (iii) or a mixture of said polymers, and
    (v) optionally conventional auxiliary substances.

2. Antacid preparation according to claim 1, wherein the acid-binding active constituents are selected from magnesium hydroxide, magnesium oxide, magnesium carbonate, magnesium silicate, aluminum hydroxide, aluminum phosphate and magnesium aluminum silicate or mixtures thereof.

3. Antacid preparation according to claim 2, wherein the effervescent mixture that releases $CO_2$ contains an acid constituent as well as a basic constituent.

4. Antacid preparation according to claim 3, wherein the acid constituent of the $CO_2$ effervescent mixture is selected from citric acid, tartaric acid, adipic acid, ascorbic acid, malic acid, fumaric acid, maleic acid, potassium bitartrate, primary sodium phosphate, primary sodium citrate, primary sodium tartrate or acid salts of basic amino acids and mixtures thereof, and the basic constituent of the $CO_2$ effervescent mixture is selected from sodium hydrogen carbonate, sodium carbonate, calcium carbonate and mixtures thereof.

5. Antacid preparation according to claim 1, wherein the swelling and gel-forming polymers are selected from a group consisting of gum tragacanth, galactomannan, methyl-cellulose, hydroxypropylmenthyl cellulose, and hydroxybutylmethyl cellulose.

6. Antacid preparation according to claim 1, wherein the concentration of the acid-binding active constituents is 20 to 80 wt. %, of the effervescent mixture, that releases $CO_2$ is 5 to 50 wt. %, of the polymeric surfactant is 0.5 to 30 wt. %, and of the swelling and gel-forming polymer is 3 to 30 wt. %, referred to total dry weight of the preparation.

7. Antacid preparation according to claim 1, wherein the preparation is formulated in the form of a chewable tablet.

8. Process for the production of the antacid preparation according to claim 1, comprising the following steps:
    (i) homogeneous mixing of the acid-binding active constituent or mixtures thereof with a basic constituent of the effervescent mixture that releases $CO_2$, as well as optionally with One or more swelling, gel-forming polymers,
    (ii) production of an aqueous solution/suspension comprising the polymeric surfactant selected from said poloxamers, as well as optioally comprising the swelling, gel-forming polymer or mixtures of said polymers,
    (iii) combing and mixing of the homogeneous mixture obtained in (i) with the solution/suspension obtained in (ii), wet granulation of the mixture, as well as drying and screening of the granules obtained,
    (iv) production of a homogeneous dry mixture from acid constituent of the $CO_2$ effervescent mixture and optionally the mixture comprises one or more said swelling, gel-forming polymers,
    (v) mixing of the mixture obtained in (iv) with the granules obtained in (iii) and optionally pressing of The granules obtained into tablets,
    wherein the swelling, gel-forming polymer is homogeneously mixed in at least one of the stages (i), (ii), or (iv) and wherein conventional auxiliary substances can also be added in the individual process steps.

9. Process according to claim 8, wherein the tablets are compressed sufficiently hard so that they are still easily chewable.

10. A method for regulating hyperacidity of gastric juices by ingesting an antacid preparation according to claim 1, wherein the preparation is formulated into an orally acceptable form.

11. Antacid preparation according to claim 1, wherein the swelling and gel-forming polymers are selected from polysaccharides and polyacrylic acids.

* * * * *

UNITED STATES PATENT AND TRADEMARK OFFICE
CERTIFICATE OF CORRECTION

PATENT NO.     : 6,589,507 B1
DATED          : July 8, 2003
INVENTOR(S)    : Kurt H. Bauer It is certified that error appears in the above-identified patent and that said Letters Patent is hereby corrected as shown below:

<u>Column 8,</u>
Line 24, delete the word, "One" with the capital letter "O", and insert therefor, the word -- one -- using all lower case letters.
Line 32, delete the word, "combing" and insert therefor, -- combining --.
Line 41, delete the word, "The" with the capital letter "T", and insert therefor, the word -- the -- using all lower case letters.

Signed and Sealed this

Eleventh Day of November, 2003

JAMES E. ROGAN
*Director of the United States Patent and Trademark Office*